United States Patent [19]

Elfert et al.

[11] 4,115,465
[45] Sep. 19, 1978

[54] SEPARATION OF AROMATIC HYDROCARBONS FROM MIXTURES, USING POLYURETHANE MEMBRANES

[75] Inventors: Klaus Elfert; Hans Jürgen Rosenkranz; Hans Rudolf, all of Krefeld, Germany

[73] Assignee: Bayer Aktiengesellschaft, Leverkusen, Germany

[21] Appl. No.: 800,812

[22] Filed: May 26, 1977

[30] Foreign Application Priority Data

Jun. 19, 1976 [DE] Fed. Rep. of Germany ....... 2627629

[51] Int. Cl.$^2$ .............................................. C07C 7/01
[52] U.S. Cl. ................................. 260/674 R; 208/308
[58] Field of Search .................... 260/674 R; 208/308

[56] References Cited

U.S. PATENT DOCUMENTS

| | | | |
|---|---|---|---|
| 2,970,106 | 1/1961 | Binning et al. | 260/674 R |
| 3,370,102 | 2/1968 | Carpenter et al. | 260/674 R |
| 3,776,970 | 12/1973 | Strazik et al. | 260/674 R |

*Primary Examiner*—Delbert E. Gantz
*Assistant Examiner*—C. E. Spresser
*Attorney, Agent, or Firm*—Burgess, Dinklage & Sprung

[57] ABSTRACT

A process for separating an aromatic hydrocarbon of the general formula

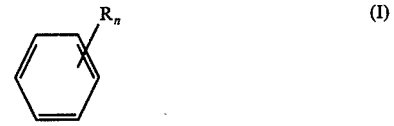

wherein
R represents an alkyl group having 1 to 3 carbon atoms and
n is 0, 1, 2, or 3 (and wherein the groups R, when n is 2 or 3 can be the same or different), from a mixture comprising said compound and one or more aliphatic hydrocarbon, cycloaliphatic hydrocarbon, alcohol, ether, ketone or a carboxylic acid ester which comprises contacting said mixture with a polyurethane membrane.

26 Claims, No Drawings

SEPARATION OF AROMATIC HYDROCARBONS FROM MIXTURES, USING POLYURETHANE MEMBRANES

The invention relates to a process for separating aromatic hydrocarbons from mixtures with other organic compounds, using polyurethane membranes.

It is already known from U.S. Pat. No. 2,953,502 substantially to separate off benzene from an azeotropic mixture of benzene and methanol by means of a nonporous plastic membrane made of polyethylene and to enrich the benzene in the phase which has permeated.

It is also known from U.S. Pat. No. 3,767,970 to separate off styrene from a mixture of styrene and ethylbenzene with the aid of a semi-permeable membrane made of specific polyurethane elastomers and to enrich the styrene in the phase which has permeated.

It has now been found, according to the present invention, that aromatic hydrocarbons of the formula (I)

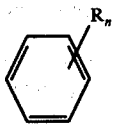

(I)

in which
R represents an alkyl group with 1 to 3 carbon atoms and
n is 0, 1, 2 or 3 (and wherein the groups R, when n is 2 or 3, can be the same or different)
can be separated from a mixture comprising the compound I with one or more of an aliphatic hydrocarbon, a cycloaliphatic hydrocarbon, an alcohol, an ether, a ketone and a carboxylic acid ester, by a process which comprises contacting the said mixture with a membrane prepared from a polyurethane.

Methyl, ethyl, propyl and isopropyl may be mentioned as examples of alkyl with 1 to 3 carbon atoms.

Compounds of general formula (I) for which the process of the invention is especially suitable are benzene, toluene, xylene, ethylbenzene and cumene.

Among those compounds from which the compounds of general formula (I) can be separated are: aliphatic, straight-chain and branched hydrocarbons with up to 14 carbon atoms, such as n-hexane, n-heptane, 2-methyl- and 5-methyl-hexane, 2,2-dimethylpentane, 2,4-dimethylpentane, 2,2,3-trimethylbutane and i-octane; cycloaliphatic hydrocarbons, especially those with 5 and 6 ring carbon atoms, which can also be substituted by alkyl with up to 8 carbon atoms, especially by $C_1$ to $C_6$-alkyl and in particular by methyl and ethyl; methylcyclopentane, cyclohexane and methylcyclohexane may be mentioned in particular; aliphatic and cycloaliphatic alcohols which correspond to the abovementioned hydrocarbons, especially lower aliphatic alcohols such as methanol, ethanol, propanol, isopropanol, butanol, isobutanol, tert.-butanol and ethylene glycol; aliphatic and cycloaliphatic ethers which are derived from the abovementioned hydrocarbons, especially tetrahydrofuran and dioxane; lower (i.e. $C_1$ to $C_6$) aliphatic and cycloaliphatic ketones, such as acetone, methyl ethyl ketone and cyclohexanone; and esters of lower ($C_1$ to $C_6$) aliphatic carboxylic acids with lower ($C_1$ to $C_6$) aliphatic alcohols, such as ethyl acetate.

The process according to the invention can be used particularly advantageously for separating the compounds of general formula (I) from aliphatic and alicyclic straight-chain or branched hydrocarbons with 5 to 8 carbon atoms. Mixtures of this type are obtained, above all, from the processing of mineral oil.

Further, the process according to the invention can be employed particularly advantageously for separating azeotropic mixtures of compounds of the formula (I) with one or more of the other compounds mentioned or for separating mixtures of compounds of the formula (I) with other compounds of a type which cannot be separated, or can be separated only with considerable difficulty, by other processes, for example which, because the boiling points are close together, cannot be separated or can be separated only with considerable difficulty by distillation.

The process according to the invention can be carried out in accordance with the known state of the art in the field of separation, using membranes.

According to the invention, the membranes used are prepared from polyurethanes; polyurethanes which can be used for this purpose, and the preparation thereof, are in themselves known.

Polyurethanes are generally prepared by reacting dihydroxy or polyhydroxy compounds of relatively high molecular weight (for example polyesters or polyethers with a molecular weight of about 500 to 5,000 and melting points of, preferably, less than 60° C.) and aliphatic, araliphatic or aromatic diisocyanates or polyisocyanates, optionally with so-called chain propagation agents, that is to say compounds of low molecular weight (molecular weight of, for example, 18 to 400) which have 2 or more groups which are reactive to isocyanate (for example diols, diamines and amino-alcohols of low molecular weight), or corresponding mixtures of these chain propagation agents, in a single stage or multistage process, in the melt or in solvents, by a large number of known processes, which can be modified.

Examples of starting materials which may be mentioned are: polyesters of carboxylic acid and aliphatic dicarboxylic acids with 2 to about 10 C atoms, preferably of adipic acid and sebacic acid, with aliphatic dialcohols with 2 to about 10 C atoms, preferably those with more than 5 C atoms, in which case the dialcohols can also be employed in order to lower the melting point of the polyester in the mixture; polyesters of low-molecular weight aliphatic lactones and ω-hydroxycarboxylic acids, preferably of caprolacton and ω-hydroxycapric acid; and also polyalkylene ether-diols, in particular polytetramethylene ether-diols, polytrimethylene ether-diols and polypropylene glycol and corresponding copolyethers.

The diisocyanates used are preferably aromatic diisocyanates, such as toluylene diisocyanate and m-xylylene diisocyanate, araliphatic diisocyanates, such as diphenylmethane 4,4'-diisocyanate, and aliphatic and cycloaliphatic diisocyanates, such as hexamethylene diisocyanate and dicyclohexylmethane 4,4'-diisocyanate.

These starting materials can also optionally be reacted with dialcohols, which are additionally employed, to give so-called prepolymers, and these can then be further polymerised with further dihydroxy or polyhydroxy compounds and diisocyanates or polyisocyanates and, optionally, further chain propagation agents.

In addition to the two-dimensionally crosslinked polyurethanes obtainable by the use of diols and diisocyanates, three-dimensionally crosslinked polyurethanes can also be obtained when triols and polyols and/or triisocyanates and polyisocyanates are at the same time employed as starting materials for the polymerisation.

Three-dimensional crosslinking can also be achieved if two-dimensionally crosslinked polyurethanes which still contain free hydroxyl groups and/or isocyanate groups are subsequently further reacted with trifunctional alcohols and/or isocyanates.

Three-dimensionally crosslinked polyurethanes of this type can likewise be obtained by subsequent reaction of two-dimensionally crosslinked polyurethanes having free isocyanate end groups with small amounts of polymers having end groups containing reactive hydrogen atoms, such as formaldehyde resins and melamine resins.

According to the invention, film-forming elastic polyurethanes which are prepared as so-called single component PUR with a characteristic value (equivalents) NCO/OH or NCO/(OH + $NH_2$) of greater than 1.0, say in the range of 1.02 to 1.1, are preferably used.

The diols employed are, in particular, butane-1,4-diol polyadipate, hexamethylene 1,6-glycol polyadipate and hexane-1,6-diol polycarbonate, the preparation of which is known, for example from DT-AS (German Published Specification) 915,908.

Diisocyanates which can be used are, preferably, isophorone diisocyanate, 4,4'-diisocyanato-diphenylmethane and toluylene diisocyanate. The chain propagation agents used are, preferably, ethylene glycol, butane-1,4-diol, ethanolamine and diamino-dicyclohexylmethane.

This group also includes polyurethanes which are prepared from a prepolymer having free hydroxyl groups, a diol and a diisocyanate with a characteristic value NCO/OH of approximately 1.

A further preferred group of film-forming polyurethanes of this type comprises so-called two-component PUR i.e. one of the abovementioned polyurethanes which has been crosslinked by subsequent further polymerisation with a polyol, such as trimethylolpropane, and, optionally, a chain propagation agent, such as 1,3-butylene glycol, and a diisocyanate. This group of two-component PUR also includes those polyurethanes which have subsequently been further crosslinked with formaldehyde resins or melamine resins.

These film-forming polyurethanes which are preferably to be used are known and commercially available. They are used, for example, for textile coating. Their preparation is described, for example, in German Patent Specification No. 831,772, DT-AS (German Published Specification) 1,694,080, DT-OS (German Published Specification) 2,221,798 and DT-OS (German Published Specification) 2,302,564 the disclosures of which are hereby specifically incorporated therein by reference.

Of course, other polyurethanes can also be employed for the preparation of membranes of the type used in the process according to the invention. The only polyurethanes which are not suitable are those which are soluble in the mixtures to be separated by the process according to the invention, so that the membrane, itself dissolves.

The process according to the invention can be carried out in accordance with known techniques in the art of separation with the aid of membranes (compare Membranes in Separation, New York, 1975, ISBN 0-471-93 268 X) the disclosures of which are hereby specifically incorporated herein by reference. In particular, the technique known as "Pervaporation" (page 99 to 116), in which non-porous, semi-permeable membranes (page 434 to 450) are used, is of special interest. Such membranes which are prepared from polymers are already in use on a large scale for the desalination of water by reverse osmosis and their preparation and industrial use are well known (pages 434 to 450 and 468 to 484).

The membranes for use according to the invention can be prepared in a known manner from casting or spinning solutions by casting films or by spinning to give tubing or hollow fibres.

Thermoplastic polyurethanes can be brought into the desired membrane form by the known methods of thermoplastic processing technology, such as extruding, calendering or injection moulding.

These manufacturing processes are well known in the art.

In general, thinner membranes permit higher rates of permeation. Therefore, membranes which are as thin as possible are preferably used in the process according to the invention.

However, as is known, the membranes must have adequate strength and stability so that they can be handled and no fractures or weak points arise during use. Preferably, therefore, the thickness of the membranes according to the invention is about 0.5 to 500μ and in particular 10 to 100μ.

It is known to support membranes of this type by means of porous supports so that they may withstand mechanical stress. The supports known in the art can be used, in the appropriate structural forms, for the process according to the invention.

It is also known to use the membranes in the form of films, tubes, tubing or hollow fibres in order to increase the surface area and, in order to achieve a maximum membrane surface area with an apparatus volume which is as small as possible, to use special apparatuses which have as small as possible an apparatus volume as separation units. Separation units of this type, which are also termed "modules", are known.

The process according to the invention can also be carried out in accordance with the known state of the art.

For this purpose the mixture to be separated, that is to say the "charge", is brought into contact with the whole of one side of the membrane and, on the other side, that is to say the "side of the permeated phase", the "permeated phase", which is either a pure component of the charge mixture or a mixture enriched in one or more components, is withdrawn in the liquid and/or gaseous form.

The material transport through the membrane is effected in known manner under a driving force and, in the process according to the invention, in general as a result of a difference in pressure. For example, a pressure which is higher than normal pressure can be chosen on the charge side and/or a pressure which is lower than normal pressure can be chosen on the side of the permeated phase.

The pressure difference can be varied within wide limits and in general is limited only by the strength of the membrane and the separation apparatus used. For example, it is possible to work under normal pressure and, optionally, the hydrostatic pressure of the liquid mixture on the charge side and under a reduced pressure of down to 0.01 bar on the side of the permeated phase and in this case the permeated phase is generally withdrawn in the vapor form and subsequently condensed. This procedure is known as "pervaporation".

However, one can also work under pressure conditions such that the permeated phase is obtained as a liquid. Likewise, it is possible for the mixture to be separated to be brought into contact not as a liquid but as a vapor with the charge side of the membrane.

The process according to the invention can be carried out within a wide temperature range. In general, the process is carried out in the range of 0° to 100°, and preferably of 20° to 60° C.

The process according to the invention can be carried out, as known in the art, both discontinuously and continuously and, likewise, in one stage or several stages, for example, in the form of a separation cascade with any desired number of separating stages.

The technical advance of the process according to the invention lies in the fact that this process for the first time enables aromatic hydrocarbons to be separated from a mixture with aliphatic hydrocarbons.

The Examples which follow, and in which Examples 1 to 10 illustrate membrane production, give evidence of the practicability and technical advance of the process according to the invention. Experimental procedures known in the art were used.

EXAMPLE 1

The polyurethane used was prepared from 21.9 parts by weight of hexane-1,6-diol polycarbonate (average molecular weight about 2,000); 5.4 parts by weight of isophorone diisocyanate and 2.7 parts by weight of diamino-dicyclohexyl-methane.

a. A 30% strength solution (weight/volume) of the polyurethane in a mixture of toluene, isopropyl acetate and ethylglycol acetate (1:1:1) was filtered through a pressure filter and left to stand until it was free from bubbles.

Films of different thicknesses were spread onto glass plates using a film spreader with an adjustable slit width. After evaporation of the solvent, the film was peeled off the glass plate and its average thickness was determined by averaging values measured in the customary manner at different points.

b. In the same manner as described under (a), a film with a thickness of about 250μ was spread onto a glass plate and the solvent was allowed to evaporate for one hour at room temperature. The glass plate, with the film spread thereon, was then placed in a methanol bath for 2 hours.

After this time the film had completely peeled off the plate. After evaporation of the methanol and after the film had been dried, the latter was measured as described above under (a) and its thickness was determined.

EXAMPLE 2

The polyurethane used was prepared from 71.4 parts by weight of a butane-1,4-diol polyadipate (average molecular weight about 2,250); 22.5 parts by weight of 4,4'-diisocyanatodiphenylmethane; 5.4 parts by weight of butane-1,4-diol; 0.7 part by weight of tetra-propyl- and -isopropyl-diphenyl-carbodiimide respectively and 0.2 part by weight of ethylene bis-stearic acid amide.

30 parts by weight of this polyurethane were dissolved in 70 parts by volume of a mixture of dimethylformamide and methyl ethyl ketone (3:2).

Films of different thicknesses were prepared from this solution as described in Example 1(a).

EXAMPLE 3

The polyurethane used was prepared from 1 mol of a prepolymer obtained from 2 mols of butane-1,4-diol polyadipate (molecular weight about 900) and 1 mol of toluylene diisocyanate (aveage molecular weight about 2,000); 3 mols of ethylene glycol and 4 mols of diphenylmethane 4,4'-diisocyanate.

30 parts by weight of this polyurethane were dissolved in 75 parts by volume of a mixture of equal parts of dimethylformamide and methyl ethyl ketone and films of different thickness were prepared from this solution as in Example 1(a).

EXAMPLE 4

The polyurethane used was prepared from 0.53 mol of hexanediol polycarbonate (average molecular weight about 2,000); 0.47 mol of butane-1,4-diol polyadipate (molecular weight about 2,250); 3 mols of butane-1,4-diol and 4 mols of 4,4'-diisocyanatodiphenylmethane.

30 parts by weight of this polyurethane were dissolved in 70 parts by volume of a mixture of dimethylformamide and methyl ethyl ketone (3:2) and films of different thicknesses were prepared from this solution as in Example 1(a).

EXAMPLE 5

The polyurethane used was prepared from 1.00 mol of butane-1,4-diol polyadipate (average molecular weight about 2,250); 4.56 mols of ethylene glycol; 0.24 mol of butane-1,4-diol and 5.80 mols of 4,4'-diisocyanato-diphenylmethane.

30 parts by weight of this polyurethane were dissolved in 70 parts by volume of a mixture of dimethylformamide and methyl ethyl ketone (3:2) and films of different thicknesses were prepared from this solution as described in Example 1(a).

EXAMPLE 6

The polyurethane used was prepared from 1.0 mol of butane-1,4-diol polyadipate (average molecular weight about 2,250); 2.5 mols of ethylene glycol; 0.5 mol of ethanolamine and 4.0 mols of 4,4'-diisocyanato-diphenylamine.

30 parts by weight of this polyurethane were dissolved in 70 parts by volume of a mixture of dimethylformamide and methyl ethyl ketone (3:2) and films of different thicknesses were prepared from this solution as in Example 1(a).

EXAMPLE 7

One gram of a solution of 60.2 parts by weight of a mixture of 2,4- and 2,6-diisocyanatotoluene, 10.1 parts by weight of trimethylolpropane, 6.2 parts by weight of 1,3-butylene glycol and 25.5 parts by weight of ethyl acetate and one gram of a solution of 315.00 parts by weight of dichloroethane, 315.00 parts by weight of ethyl acetate, 49.00 parts by weight of a diurethane obtained from methyldiethanolamine and phenyl isocyanate, 21.00 parts by weight of titanium tetra-stearate, 14.00 parts by weight of acetic acid and 1.75 parts by weight of acetic anhydride were added to 100 g of the polyurethane solution prepared according to Example 2.

a. Films of different thicknesses were spread from this solution onto glass plates using a film spreader with an adjustable slit width and the films were dried for 1 hour at 140° C. The film was then peeled off the glass plate and its average thickness was determined by averaging the values measured in the customary manner at different points.

EXAMPLE 8

One gram of each of the additives described in Example 7 was added, as in Example 7, to 100 g of the polyurethane solution prepared according to Example 3 and films of different thicknesses were prepared from this solution as described in Example 7(a).

EXAMPLE 9

One gram of a 50% strength solution of a melamine-formaldehyde resin in isobutanol and 0.1 g of a solution of 20 g of N-methyl-morpholine toluenesulphonate in 64 g of water and 16 g of isopropanol were added to 100 g of the polyurethane solution prepared according to Example 1 and films were prepared from this solution analogously to Example 7(a).

EXAMPLE 10

The polyurethane used had been obtained as follows: A polyester obtained from 7.2 mols of hexamethylene 1,6-glycol and 5.35 mols of adipic acid was reacted with 1 mol of toluylene diisocyanate to give a prepolymer.

82.4 parts by weight of this prepolymer were then reacted with 17.6 parts by weight of toluylene diisocyanate to give a polyurethane.

5% by weight, relative to the total mixture of a polyurethane obtained from 14.7 parts by weight of trimethylolpropane, 6.3 parts by weight of butane-1,3-diol and 79.0 parts by weight of toluylene diisocyanate and 5% by weight, relative to the total mixture of a solution of 315.00 parts by weight of dichloroethane, 315.00 parts by weight of ethyl acetate, 49.00 parts by weight of a diurethane obtained from methyldiethanolamine and phenyl isocyanate, 21.00 parts by weight of titanium tetra-stearate, 14.00 parts by weight of acetic acid and 1.7 parts by weight of acetic anhydride were added to a 30% by weight solution of this polyurethane in ethyl acetate and films were prepared from the solution thus obtained and these were dried for 1 hour at 140° to 150° C.

EXAMPLES 11 to 36

In order to determine the permeation data of the membranes prepared as described in Examples 1 to 10 there was used a measuring apparatus comprising two parts which can be screwed together, the upper half of which consisted of a cylindrical chamber with a capacity of 300 ml, into which the mixture to be separated, that is to say the charge, was filled. The lower part of the apparatus was an approximately hemispherical cover with a small volume and an outlet pipe.

The membrane to be tested was supported on the side of the permeated phase by a sintered metal plate. The seal in the apparatus was effected by Teflon sealing rings between the upper part and the membrane and between the sintered plate and the lower part of the apparatus.

The charge side of the membrane was under the hydrostatic pressure of the charge liquid at atmospheric pressure and the phase which permeated was continuously withdrawn by suction on the permeated phase side of the membrane. For this purpose, the outlet pipe of the apparatus was connected by a line, via three cold traps which were arranged in series and were cooled with a solid carbon dioxide/acetone mixture, to a vacuum pump.

The phase which had permeated was virtually completely condensed in the cold traps. The pressure on the side of the permeated phase was measured between the cold traps and the vacuum pump and was only a few mm Hg; the pressure value, which varied in the individual Examples, apparently depended essentially on the degree of tightness achieved in the apparatus.

The effective surface area of the membrane was 39.6 $cm^2$.

The individual experiments were carried out for different lengths of time varying between 0.5 and 7 hours.

In order to compensate for the changes in the concentration of the liquid mixture to be separated which arose when the test time was prolonged, the condensed permeated phase was recycled, after taking a sample for analysis, at specific intervals into the charge and mixed.

The membranes of different thicknesses prepared according to Examples 1 to 10 were used for carrying out the following Examples; the mixtures to be separated were warmed to a temperature of 25° C. and kept at this temperature.

Table I which follows gives:
1. No. of the Example
2. The nature of the membrane, characterised by the number of the example according to which it was prepared
3. The thickness of the membrane in $\mu$
4. The constituents of the mixture to be separated
5. The composition (% by weight)
   a. of the charge and
   b. of the phase which permeated
6. The rate of permeation
7. The separation factor $\alpha$ and
8. The pressure on the side of the permeated phase, in mm Hg for the individual Examples.

The separation or enrichment achieved is given by the separation factor $\alpha$ which is a measure of the selective permeability of the membrane; it is calculated according to the following equation $$\alpha = (C_{Ap}/C_{Bp}) \times (C_{Bg}/C_{Ag})$$

in which $C_{Ap}$ and $C_{Bp}$ denote the concentrations of A and B in the phase which has permeated and $C_{Ag}$ and $C_{Bg}$ denote the corresponding concentrations in the mixture to be separated and A in each case denotes the component which is to be separated off from the mixture and B denotes the other component or components of the mixture.

The rate of permeation is given as a measure of the speed of separation or the time required for separation; i.e. the amounts, in grams, of permeated phase obtained in an individual experiment are converted to give the amounts for a membrane surface of 1 $m^2$ and a test time of 1 hour.

Table 1

| Example No. | Membrane prepared according to Example No. | Thickness [μ] | Constituents of the mixture | Composition (% by weight) Charge | Composition (% by weight) Permeate | Rate of permeation [g/m²hour] | α | Vacuum [mm Hg] |
|---|---|---|---|---|---|---|---|---|
| 11 a | Example 1 a) | 46 | B (benzene) / C (cyclohexane) | 10 / 90 | 40 / 60 | 91 | 6 | 1.5 |
| 11 b | Example 1 a) | 46 | B / C | 20 / 80 | 54 / 46 | 146 | 4.7 | 1.5 |
| 11 c | Example 1 a) | 46 | B / C | 30 / 70 | 63 / 37 | 360 | 4 | 1.5 |
| 11 d | Example 1 a) | 46 | B / C | 50 / 50 | 80 / 20 | 1,290 | 4 | 1.5 |
| 11 e | Example 1 a) | 46 | B / C | 70 / 30 | 85 / 15 | 2,480 | 2.4 | 1.2 |
| 11 f | Example 1 a) | 46 | B / C | 80 / 20 | 91 / 9 | 3,740 | 2.5 | 1.2 |
| 11 g | Example 1 a) | 46 | B / C | 90 / 10 | 96 / 4 | 4,530 | 2.7 | 1.2 |
| 12 a | Example 1 a) | 16 | B / C | 10 / 90 | 40 / 60 | 71 | 6 | 4 |
| 12 b | Example 1 a) | 16 | B / C | 20 / 80 | 53 / 47 | 207 | 4.5 | 4 |
| 12 c | Example 1 a) | 16 | B / C | 30 / 70 | 63.5 / 36.5 | 585 | 4.1 | 5 |
| 12 d | Example 1 a) | 16 | B (benzene) / C (cyclohexane) | 50 / 50 | 80 / 20 | 1,800 | 4 | 5 |
| 12 e | Example 1 a) | 16 | B / C | 70 / 30 | 84 / 16 | 4,500 | 2.25 | 5 |
| 12 f | Example 1 a) | 16 | B / C | 80 / 20 | 91 / 9 | 7,000 | 2.5 | 5 |
| 12 g | Example 1 a) | 16 | B / C | 90 / 10 | 93 / 7 | 10,000 | 1.5 | 5 |
| 13 | Example 1 a) | 16 | benzene / methylcyclopentane / cyclohexane | 80 / 15 / 5 | 91 / 9 } | 7,025 | 2.5 | 6 |
| 14 | Example 1 a) | 28 | toluene / cyclohexane | 50 / 50 | 76 / 24 | 747 | 3.2 | 12 |
| 15 a | Example 1 a) | 52 | benzene / dioxane | 70 / 30 | 76 / 24 | 3,171 | 1.4 | 12 |
| 15 b | Example 1 a) | 52 | benzene / ethyl acetate | 70 / 30 | 80 / 20 | 3,233 | 1.7 | 12 |
| 16 a | Example 1 b) | 41 | B (benzene) / C (cyclohexane) | 20 / 80 | 58 / 42 | 76 | 5.5 | 0.5 |
| 16 b | Example 1 b) | 41 | B / C | 30 / 70 | 73 / 27 | 217 | 6.3 | 1.5 |
| 16 c | Example 1 b) | 41 | B / C | 50 / 50 | 90 / 10 | 480 | 9 | 1.5 |
| 16 d | Example 1 b) | 41 | B / C | 70 / 30 | 96 / 4 | 1,360 | 10 | 4 |
| 16 e | Example 1 b) | 41 | B / C | 80 / 20 | 97 / 3 | 2,540 | 8 | 4 |
| 16 f | Example 1 b) | 41 | B / C | 90 / 10 | 99 / 1 | 4,150 | 11 | 4 |
| 17 a | Example 2 | 42 | B (benzene) / C (cyclohexane) | 30 / 70 | 52 / 48 | 1,100 | 2.5 | 1.6 |
| 17 b | Example 2 | 42 | B / C | 50 / 50 | 71.5 / 28.5 | 1,100 | 2.5 | 1.3 |
| 17 c | Example 2 | 49 | B / C | 70 / 30 | 88 / 99.5 12 | 995 | 3.1 | 1.5 |
| 17 d | Example 2 | 42 | B / C | 80 / 20 | 93 / 7 | 1,280 | 3.3 | 1.5 |
| 17 e | Example 2 | 42 | B / C | 90 / 10 | 96 / 4 | 2,170 | 2.7 | 1.5 |
| 18 | Example 2 | 42 | benzene / methanol | 60.5 / 39.5 | 74 / 26 | 2,636 | 1.9 | 0.6 |
| 19 | Example 2 | 42 | benzene / ethanol | 67.6 / 32.4 | 79 / 21 | 2,350 | 1.8 | 0.6 |
| 20 | Example 2 | 42 | benzene / isopropanol | 66.7 / 33.3 | 85.5 / 14.5 | 1,792 | 2.95 | 10 |
| 21 | Example 3 | 45 | benzene / cyclohexane | 90 / 10 | 99.5 / 0.5 | 250 | 22 | 0.8 |
| 22 | Example 3 | 33 | toluene / cyclohexane | 90 / 10 | 99 / 1 | 267 | 11 | 11 |
| 23 | Example 3 | 26 | benzene / methanol | 60.5 / 39.5 | 71 / 29 | 2,835 | 1.6 | 0.6 |
| 24 | Example 3 | 26 | benzene / ethanol | 67.6 / 32.4 | 77 / 23 | 1,895 | 1.6 | 0.5 |
| 25 | Example 4 | 29 | benzene / cyclohexane | 80 / 20 | 97 / 3 | 650 | 8.1 | 25 |
| 26 | Example 4 | 23 | benzene / methanol | 60.5 / 39.5 | 77 / 23 | 2,754 | 2.2 | 0.65 |
| 27 | Example 4 | 23 | benzene / ethanol | 67.6 / 32.4 | 79 / 21 | 2,302 | 1.8 | 0.65 |
| 28 | Example 5 | 21 | benzene / cyclohexane | 80 / 20 | 92 / 8 | 2,350 | 2.9 | 7 |
| 29 | Example 5 | 27 | benzene / methylcyclopentane / cyclohexane | 80 / 15 / 5 | 99.5 / 0.5 | 1,581 | 49.7 | 10 |
| 30 | Example 5 | 38 | benzene / methanol | 60.5 / 39.5 | 72 / 28 | 1,733 | 1.7 | 0.6 |
| 31 | Example 5 | 38 | benzene / ethanol | 67.6 / 32.4 | 77.5 / 22.5 | 1,205 | 1.7 | 0.6 |

Table 1-continued

| Example No. | Membrane prepared according to Example No. | Thickness [μ] | Constituents of the mixture | Composition (% by weight) Charge | Composition (% by weight) Permeate | Rate of permeation [g/m²hour] | α | Vacuum [mm Hg] |
|---|---|---|---|---|---|---|---|---|
| 32 | Example 6 | 44 | benzene | 80 | 99.5 | 626 | 49.7 | 11 |
|  |  |  | cyclohexane | 20 | 0.5 |  |  |  |
| 33 a | Example 7 | 18 | B (benzene) | 70 | 98.5 | 630 | 28.2 | 5 |
|  |  |  | C (cyclohexane) | 30 | 1.5 |  |  |  |
| 33 b | Example 7 | 18 | B | 80 | 99.5 | 990 | 49.7 | 5 |
|  |  |  | C | 20 | 0.5 |  |  |  |
| 33 c | Example 7 | 18 | B | 90 | 99.5 | 1,670 | 22 | 5 |
|  |  |  | C | 10 | 0.5 |  |  |  |
| 34 a | Example 8 | 13 | B | 80 | 99.5 | 515 | 49.7 | 12 |
|  |  |  | C | 20 | 0.5 |  |  |  |
| 34 b | Example 8 | 13 | B | 90 | 99.5 | 934 | 22 | 12 |
|  |  |  | C | 10 | 0.5 |  |  |  |
| 35 a | Example 9 | 25 | B | 30 | 84 | 600 | 12.2 | 2.5 |
|  |  |  | C | 70 | 16 |  |  |  |
| 35 b | Example 9 | 25 | B | 50 | 86 | 1,270 | 6.15 | 2.5 |
|  |  |  | C | 50 | 14 |  |  |  |
| 35 c | Example 9 | 25 | B | 70 | 92 | 3,220 | 4.9 | 2.5 |
|  |  |  | C | 30 | 8 |  |  |  |
| 35 d | Example 9 | 25 | B | 80 | 95 | 6,450 | 4.75 | 2.5 |
|  |  |  | C | 20 | 5 |  |  |  |
| 35 e | Example 9 | 25 | B | 90 | 99 | 7,560 | 11 | 2.5 |
|  |  |  | C | 10 | 1 |  |  |  |
| 36 a | Example 10 | 14 | B | 50 | 97 | 780 | 32.4 | 7 |
|  |  |  | C | 50 | 3 |  |  |  |
| 36 b | Example 10 | 14 | B | 80 | 98 | 3,400 | 12.2 | 7 |
|  |  |  | C | 20 | 2 |  |  |  |
| 36 c | Example 10 | 14 | B | 90 | 99.5 | 4,350 | 22 | 7 |
|  |  |  | C | 10 | 0.5 |  |  |  |
| 37 a | Example 10 | 10 | B (benzene) | 50 | 94 | 749 | 15.6 | 20 |
|  |  |  | H (n-hexane) | 50 | 6 |  |  |  |
| 37 b | Example 10 | 10 | B | 70 | 94 | 2,410 | 6.7 | 20 |
|  |  |  | H | 30 | 6 |  |  |  |
| 37 c | Example 10 | 10 | B | 80 | 95 | 3,970 | 4.75 | 20 |
|  |  |  | H | 20 | 5 |  |  |  |
| 37 d | Example 10 | 10 | B | 90 | 97.5 | 6,160 | 4.3 | 20 |
|  |  |  | H | 10 |  |  |  |  |

What is claimed is:

1. In a process for separating a first component from a mixture of the same with other components wherein the mixture is disposed on one side of a membrane and a higher pressure is established on the mixture side of the membrane than on the opposed side, said first component is withdrawn through said membrane to said opposed side and at least a partial vacuum is applied to the opposed side of membrane and said first membrane is withdrawn from said membrane in a vapor state, the improvement wherein:

A. the membrane is (of) an aromatic selective polyurethane membrane;

B. the first component has the formula

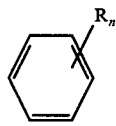

wherein R represents an alkyl group having 1 to 3 carbon atoms and $n$ is 0, 1, 2 or 3; and C. said first component is in admixture with one or more aliphatic hydrocarbon, cycloaliphatic hydrocarbon, alcohol, ether, ketone or carboxylic acid ester.

2. A process according to claim 1 wherein a compound of general formula I is separated from a mixture of that compound with an aliphatic or alicyclic straight-chain or branched hydrocarbon having 5 to 8 carbon atoms.

3. A process according to claim 1 wherein the compound of general formula I is benzene, toluene, xylene, ethylbenzene or cumene.

4. A process according to claim 1 wherein the polyurethane is a single component PUR having an (NCO/OH) or (NCO/(OH+NH$_2$) greater than 1.0.

5. A process according to claim 4 wherein the polyurethane has an (NCO/OH) or (NCO/(OH+NH$_2$) in the range 1.02 to 1.10.

6. A process according to claim 1 wherein the polyurethane is a two-component PUR.

7. A process according to claim 1 wherein the membrane has a thickness in the range 0.5 to 500μ.

8. A process according to claim 7 wherein the membrane has a thickness in the range 10 to 100μ.

9. A process according to claim 1 which is carried out at a temperature in the range 0° to 100° C.

10. A process according to claim 1 wherein the polyurethane of the membrane is the reaction product of hexane-1,6-diol polycarbonate, isophorone diisocyanate and diaminodicyclohexyl-methane.

11. A process according to claim 1 wherein the polyurethane of the membrane is one prepared from a reaction of butane-1,4-diol polyadipate, 4,4'-diisocyanato-diphenylmethane, butane-1,4-diol, tetrapropyl- or tetraisopropyl-diphenylcarbodiimide and ethylene-bis-stearic acid amide.

12. A process according to claim 1 wherein the polyurethane of the membrane is one prepared by reaction of butane-1,4-diol polyadipate, toluylene diisocyanate, ethylene glycol and diphenylmethane-4,4'-diisocyanate.

13. A process according to claim 1 wherein the polyurethane of the membrane is one prepared by reaction of hexane-diol-polycarbonate, butane-1,4-diol polyadipate, butane-1,4-diol and 4,4'-diisocyanato-diphenylmethane.

14. A process according to claim 1 wherein the polyurethane of the membrane is one prepared by reaction of butane-1,4-diol polyadipate, ethyleneglycol, butane-1,4-diol and 4,4'-diisocyanato-diphenylmethane.

15. A process according to claim 1 wherein the polyurethane of the membrane is one prepared by reaction of butane-1,4-diol polyadipate, ethylene glycol, ethanolamine and 4,4'-diisocyanato-diphenylamine.

16. A process according to claim 1 wherein the polyurethane of the membrane is one prepared by reaction of a mixture of 2,4- and 2,6-diisocyanato-toluene, trimethylol-propane, butylene glycol and ethyl acetate to which is added the reaction product of dichloroethane, ethyl acetate, a diurethane obtained from methyl-diethanolamine and phenyl isocyanate, titanium tetrastearate, acetic acid and acetic anhydride.

17. A process according to claim 10 wherein the polyurethane is one which has been treated with a solution of N-methyl-morpholine toluenesulphonate in isopropanol.

18. A process according to claim 1 wherein the polyurethane is one obtained by formation of a polyester from hexamethylene-1,6-glycol, adipic acid and toluylene diisocyanate and conversion of said prepolyester to a polyurethane by reaction thereof with additional toluylene diisocyanate.

19. A process according to claim 18 wherein said polyurethane is one additionally treated with a mixture of trimethylol propane, butane-1,3-diol, toluylene diisocyanate and a mixture of dichloroethane, ethyl acetate and a diurethane.

20. A process according to claim 1 wherein said first component is benzene and it is in admixture with hexane.

21. A process according to claim 1 wherein said first component is benzene and it is in admixture with methylcyclopentane.

22. A process according to claim 1 wherein said first component is benzene and it is in admixture with ethanol.

23. A process according to claim 1 wherein said first component is benzene and it is in admixture with methanol.

24. A process according to claim 1 wherein said first component is benzene and it is in admixture with normal hexane.

25. A process according to claim 1 wherein said first component is benzene, toluene, xylene, ethyl benzene or cumene.

26. A process according to claim 1 wherein said membrane consists essentially of polyurethane.

* * * * *

UNITED STATES PATENT AND TRADEMARK OFFICE
CERTIFICATE OF CORRECTION

PATENT NO. : 4,115,465
DATED : September 19, 1978
INVENTOR(S) : Elfert et al.

It is certified that error appears in the above-identified patent and that said Letters Patent are hereby corrected as shown below:

Column 10, Table I, Example 17c, under heading entitled Permeate, "99.5" should read -- 12 --, and under heading entitled Rate of Permeation, delete "12".

Signed and Sealed this

Sixteenth Day of January 1979

[SEAL]

Attest:

RUTH C. MASON
Attesting Officer

DONALD W. BANNER
Commissioner of Patents and Trademarks